(12) United States Patent
Causey et al.

(10) Patent No.: US 10,874,823 B2
(45) Date of Patent: Dec. 29, 2020

(54) REMOTELY CONTROLLED BILATERAL ALTERNATING TACTILE STIMULATION THERAPEUTIC METHOD AND SYSTEM

(71) Applicants: Chris Alan Causey, Tacoma, WA (US); Dakota Pellegrino, Hillsboro, OR (US)

(72) Inventors: Chris Alan Causey, Tacoma, WA (US); Dakota Pellegrino, Hillsboro, OR (US)

(73) Assignees: BLUETAPP, INC., Tacoma, WA (US); OREGON STATE UNIVERSITY, Corvallis, OR (US)

( * ) Notice: Subject to any disclaimer, the term of this patent is extended or adjusted under 35 U.S.C. 154(b) by 0 days.

(21) Appl. No.: 16/886,357

(22) Filed: May 28, 2020

(65) Prior Publication Data

US 2020/0376230 A1  Dec. 3, 2020

Related U.S. Application Data

(60) Provisional application No. 62/853,559, filed on May 28, 2019.

(51) Int. Cl.
*A61M 21/02* (2006.01)
*A61M 21/00* (2006.01)
(Continued)

(52) U.S. Cl.
CPC ......... *A61M 21/02* (2013.01); *G06F 3/04817* (2013.01); *G06F 8/60* (2013.01); *G08B 5/36* (2013.01); *G16H 20/30* (2018.01); *G16H 40/67* (2018.01); *H04L 65/1069* (2013.01); *H04L 65/4007* (2013.01); *A61M 2021/0022* (2013.01);
(Continued)

(58) Field of Classification Search
CPC ............................................. A61M 21/00–02
See application file for complete search history.

(56) References Cited

U.S. PATENT DOCUMENTS 5,619,291 A   4/1997  Putnam
6,001,073 A   12/1999  Schmidt et al.
(Continued)

OTHER PUBLICATIONS http://www.emdrkit.com/comparisonpage/?lang=en, Which EMDR Kit is best for you?, May 16, 2019.

*Primary Examiner* — Thaddeus B Cox
(74) *Attorney, Agent, or Firm* — George A. Leone; Citadel Patent Law

(57) ABSTRACT

A bilateral alternating tactile stimulation therapeutic system includes an Internet web page; a first mobile device, at a first location, configured to access the Internet web page, wherein the first mobile device has a first application for transmitting audio information and pulse control information including alternating pulsation signals for uploading to the Internet web page; a second mobile device, at a second location remote from the first location, adapted to connect to the Internet web page and having a second application for receiving the audio information and the pulse control information in a streaming or live mode; a pair of pulsating devices wirelessly coupled to the second mobile device; and wherein the second mobile device is programmed to enable a subject to hear the audio information and also transmit the alternating pulsation signals to the pair of pulsating devices.

15 Claims, 10 Drawing Sheets

(51) Int. Cl.
*G16H 40/67* (2018.01)
*G06F 8/60* (2018.01)
*G08B 5/36* (2006.01)
*H04L 29/06* (2006.01)
*G06F 3/0481* (2013.01)
*G16H 20/30* (2018.01)

(52) U.S. Cl.
CPC ............ *A61M 2021/0027* (2013.01); *A61M 2205/3553* (2013.01); *A61M 2205/3569* (2013.01); *A61M 2205/3584* (2013.01); *A61M 2205/505* (2013.01); *A61M 2205/584* (2013.01); *A61M 2205/8206* (2013.01)

(56) References Cited

U.S. PATENT DOCUMENTS

| | | | |
|---|---|---|---|
| 6,186,145 B1 | 2/2001 | Brown | |
| 6,334,778 B1 | 1/2002 | Brown | |
| 7,224,281 B2 | 5/2007 | Santos | |
| 7,853,241 B1 | 12/2010 | Harrison | |
| 9,408,997 B2 | 8/2016 | Kelley | |
| 10,175,935 B2 | 1/2019 | Derungs | |
| 2007/0191912 A1* | 8/2007 | Fischer | A61N 1/37282 607/60 |
| 2011/0118555 A1 | 5/2011 | Dhumne et al. | |
| 2014/0222102 A1* | 8/2014 | Lemus | A61N 1/36031 607/48 |
| 2015/0039047 A1* | 2/2015 | Parker | A61N 1/36071 607/46 |
| 2017/0296429 A1* | 10/2017 | Mayo | A61H 23/02 |
| 2018/0318545 A1* | 11/2018 | Jones | A61M 21/02 |
| 2019/0074093 A1* | 3/2019 | Walsh | G16H 10/20 |

\* cited by examiner

REMOTELY CONTROLLED BILATERAL ALTERNATING TACTILE STIMULATION THERAPEUTIC METHOD AND SYSTEM

TECHNICAL FIELD

The present invention relates to a method and system for providing tactile bilateral stimulation therapy. More particularly, the method and system are directed to providing a remote control internet accessible tactile bilateral stimulation therapy system operated by a therapist or using a therapy program recorded by a therapist.

BACKGROUND

Therapy sessions with PTSD clients often benefit from using a specific technology to stimulate the bilateral access required in order to get the traumatic memories moving. The same technology is used to restore equilibrium and allow the client to center themselves creating a sense of internal safety. One limitation of the existing technology when used by a therapist, is that it most often requires the client and therapist to be in the same room.

Anxiety disorders are the most common mental disorders in the United States, resulting in very large health care costs in addition to considerable disease burden; studies show that up to 33.7% of the population is affected by an anxiety disorder at some point in their lifetime (Bandelow and Michaelis 2015). Bilateral stimulation therapy (BLS) is a non-invasive, somatosensory-based therapy method which has proven effective in the treatment of anxiety related illness; the mechanism of this therapy is thought to be the modulation of the electrical activity of brain networks that mediate the stress response with some studies showing a 50%-62% reduction in stress related symptoms after treatment (Serin, Hageman and Kade, 2018). The treatment is administered by the use of a device which produces left-right alternating vibrotactile stimulation via two vibrating pods or "paddles" which are held by the patient. Currently, several BLS devices are commercially available; the devices marketed to practitioners have corded pods (held by the patient) connected to a battery-powered control box (held by the therapist) which has adjustment knobs for amplitude, frequency, and in some cases, volume controls for audio synchronization output to a headphone jack. There is also a similar market for personal use devices, mainly for stress management; these personal devices are often wearable wristbands that have integral rechargeable batteries and synchronize wirelessly with a smartphone application that provides several standard treatment routines. For either form the retail price point is between $160-180 however some with "advanced features" are priced up to $300.

One device for inducing alternating tactile simulations in a human subject was proposed in U.S. Pat. No. 6,001,073 issued to Schmidt et al. Dec. 14, 1989. That device includes a first vibrating element and a second vibrating element connected to a controller. The subject holds the first vibrating element in one hand and the second vibrating element in the other hand. When the device is activated the following occurs in sequence: the first vibrating element vibrates, pauses, the second vibrating element vibrates, pauses, the first vibrating element vibrates, pauses, the second vibrating element vibrates, pauses, and so forth, until the device is deactivated.

Unfortunately, it has been found, that vibrating elements as used in the art often become irritating to the subject. Further, the available devices do not allow for use where the therapist and subject are in different locations remote from each other.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

One particularly distressing drawback of currently available systems is that they do not provide a way for therapists to deliver bilateral alternating stimulation therapy over long distances and into remote areas. Military personnel suffering with PTSD, for example, are often located in extreme environments, including militarized zones in undeveloped countries. It would be extremely beneficial for such individuals to avail themselves of therapy utilizing BLS type protocols under such conditions. This is one of the reasons that the inventors herein have provided a new and novel remote control internet accessible therapy system as described in the claims.

A bilateral alternating tactile stimulation therapeutic system the system includes an Internet web page; a first mobile device, at a first location, configured to access the Internet web page, a first processor, onboard the first mobile device, the first processor being programmed to execute a first application for transmitting audio information and pulse control information including alternating pulsation signals for uploading to the Internet web page; a second mobile device, at a second location remote from the first location, adapted to connect to the Internet web page; a second processor, onboard the second mobile device, programmed to execute a second application for receiving the audio information and the pulse control information in a streaming or live mode; a first pair of pulsating devices wirelessly coupled to the second mobile device; and where the second processor is programmed to enable a subject to hear the audio information through the mobile device and transmit the alternating pulsation signals to the pair of pulsating devices.

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings, in which:

Figure 1:
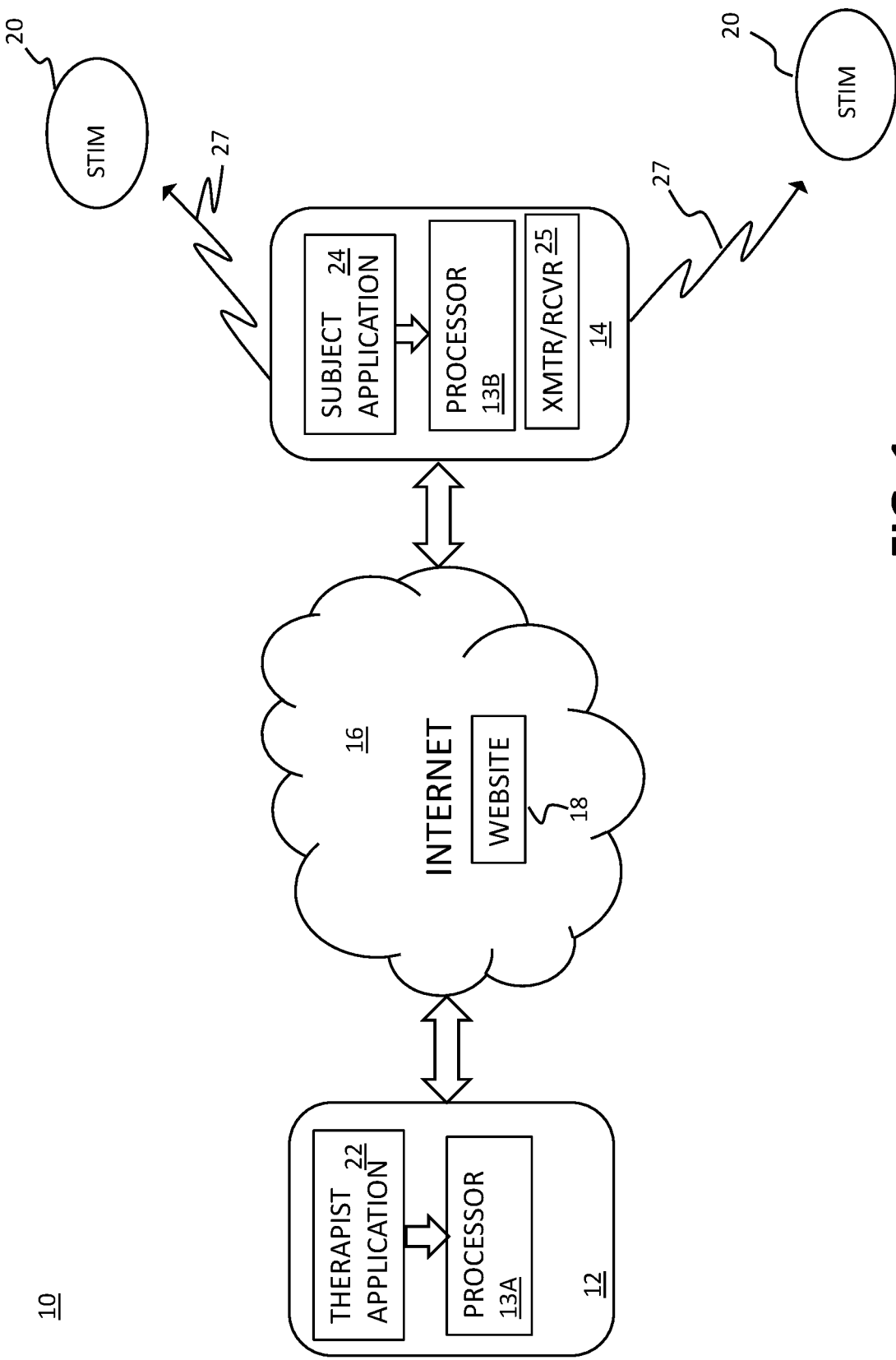
FIG. 1 schematically shows an example of a remotely controlled bilateral alternating tactile stimulation therapeutic system.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements and have been solely selected for ease of recognition in the drawings.

DETAILED DESCRIPTION

The following disclosure describes a method and system for remotely controlled bilateral alternating tactile stimulation therapy. Several features of methods and systems in accordance with example embodiments are set forth and described in the figures. It will be appreciated that methods and systems in accordance with other example embodiments can include additional procedures or features different than those shown in the figures. Example embodiments are described herein with respect to a method and system directed to an Internet based streaming of a recorded session or a live streaming mode. However, it will be understood that these examples are for illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example," "an example embodiment," "one embodiment," "an embodiment" or combinations and/or variations of these terms means that a particular feature, structure or characteristic described in connection with the embodiment or example is included in at least one embodiment or example of the present disclosure. Thus, the appearances of the phrases "in one example" or "in an example" in various places throughout this specification are not necessarily all referring to the same example embodiment or example. Furthermore, the particular features, structures, or characteristics may be combined in any suitable manner in one or more embodiments or examples.

Definitions

Generally, as used herein, the following terms have the following meanings:

The articles "a" or "an" and the phrase "at least one" as used herein refers to one or more.

"Bluetooth®" technology, as used herein means a commercially available low-power wireless connectivity technology used to stream audio, transfer data and broadcast information between devices. Bluetooth® technology is a wireless technology standard for exchanging data between fixed and mobile devices over short distances using short-wavelength UHF radio waves in the industrial, scientific and medical radio bands, for example, from 2.400 to 2.485 GHz. This technology is available from Bluetooth SIG, Inc. of Kirkland, Wash.

ANT is an ultra-low power (ULP) wireless networking protocol which enables objects from everyday life to connect with each other similar to Bluetooth® technology.

As used herein, "mobile device" has its generally accepted meaning and includes any portable device that can make and receive telephone calls to and from a public telephone network, which includes cellular telephones, and other mobile and fixed-line phones across the world. It also includes mobile devices that support a wide variety of other services such as Voice over Internet Protocol (VOIP), text messaging, software applications, MMS, e-mail, Internet access, and short-range wireless communications (for example, infrared and Bluetooth® communications).

As used herein, "tablet computer" has its generally accepted meaning and includes any mobile computer including a complete mobile computer, larger than a mobile phone or personal digital assistant, integrated into a flat touch screen and primarily operated by touching the screen such as, for example, an Apple iPad® tablet computer.

As used herein, "plurality" is understood to mean more than one. For example, a plurality refers to at least 2, 3, 4, 5, 70, or more.

As used in this specification, the terms "computer", "processor" and "computer processor" encompass a personal computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

As used herein "network" is understood to mean a digital telecommunications network which allows nodes to share resources and/or a computer network wherein computing devices exchange data with each other using data link connections between nodes. Typically these data links are established over cable media such as wires or optic cables, or wireless media such as Wi-Fi.

As used herein, the "Internet" is a computer network providing access to the World Wide Web, digital video, digital audio, shared use of application and storage servers, printers, and fax machines, and use of email and instant messaging applications as well as many others.

"Obtaining" is understood herein as manufacturing, purchasing, or otherwise coming into possession of.

As used herein "remote" is understood as meaning separated by a distance beyond the typical range of a fixed location Bluetooth® signal, in a different building, in a different country or out of the line of sight of a selected mobile device.

Example Embodiments

The remotely controlled bilateral alternating tactile stimulation therapeutic system disclosed herein has several advantages over known systems. For the first time, it enables a therapist to live stream a therapy session including alternating tactile bilateral stimulation to a subject over the Internet so that the therapist and subject need not be in the same room or even in the same country. In another advantage, the disclosed system and method enables a subject to download a prerecorded therapy session into a mobile device, allowing the subject to self-conducted therapy session when unable to access the Internet.

Referring now to FIG. 1, an example of a remotely controlled bilateral alternating tactile stimulation therapeutic system is schematically shown. A bilateral alternating tactile stimulation therapeutic system 10 includes a first mobile device 12, a second mobile device 14, and a pair of pulsating devices 20. Each of the first and second mobile devices 12, 14 are adapted to wirelessly couple to the Internet 16. Residing in the Internet 16 is a dedicated website 18. The website 18 may include computer software programs, typically called applications, which may be uploaded and downloaded through the first and second mobile devices 12, 14 and other known systems or devices such as personal computers. The applications are described hereinbelow in relation to touchscreen activation icons representing the various applications that are executed by an onboard processor.

In one useful example, a professional, such as a therapist, may download a therapist application 22 from the website 18 to program an onboard processor 13A. A subject, such as a client of the therapist, using the second mobile device may download a subject application 24 from the website 18 to program a second onboard processor 13B. The downloaded applications reside in the first and second onboard processors 13A, 13B so that the processors are programmed to allow interactions between the first and second mobile devices including voice and video communications and control signals for the pulsating devices, as explained in more detail below.

In one example, the therapist application 22 programs the processor to provide audio, video, and control signals to pulsating devices through the Internet website 18 as transmitted by the therapist. The subject application 24 provides control signals for controlling a transmitter/receiver 25. Transmitter/receiver 25 receives radiofrequency control signals from the Internet and transmits radiofrequency control signals, such as Bluetooth® generated signals, to the pair of pulsating devices 20. The system may be used by real-time streaming or live through the website or another communications website. In an alternate example, the subject may download a pre-recorded session from the website and play it whether or not connected to the Internet.

Figure 2:
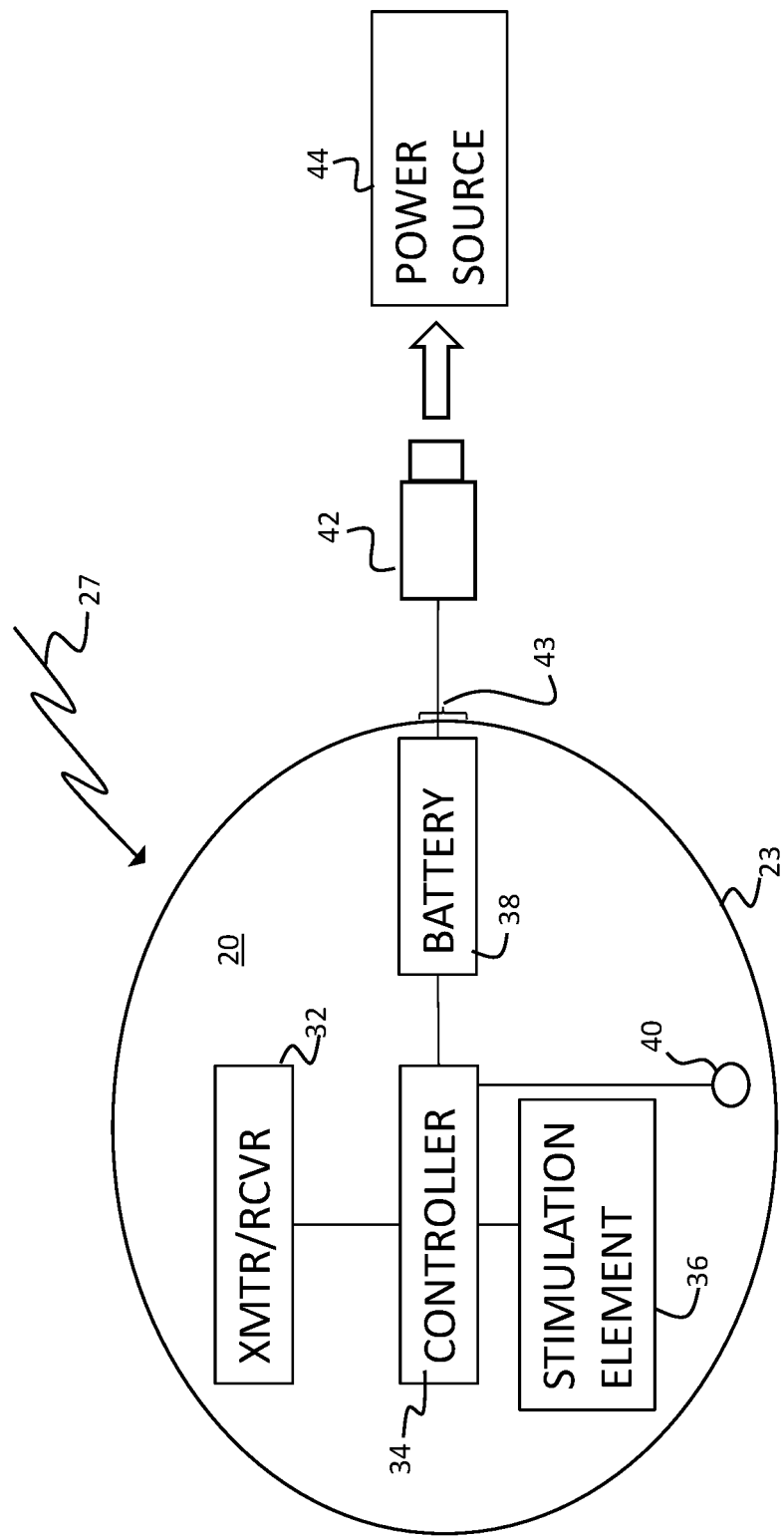
FIG. 2 schematically shows an example of a pulsating device as used in a remotely controlled bilateral alternating tactile stimulation therapeutic system.

Referring now to FIG. 2, an example of a pulsating device as used in a remotely controlled bilateral alternating tactile stimulation therapeutic system is schematically shown. Each pulsating device 20 comprises a transmitter/receiver 32, a controller 34, a rechargeable battery 38, a stimulation element 36 and a status light 40. The transmitter/receiver 32 may be a Bluetooth® transmitter/receiver, but may also be another dedicated RF transmitter/receiver. The controller 34 may comprise a microprocessor or the like programmed to receive signals from the transmitter/receiver 32 and translate them into control signals for the stimulation element 36 and the indicator light 40. The battery 38 is coupled to supply power to each of the components either directly or through the controller 34. The battery 38 is advantageously rechargeable by connection to an electrical connector 43 which is adapted to accept, for example, a power cord such as a USB connector 42. When recharging, the USB connector may connect the battery to a power source 44, such as a computer USB port or the like.

In one useful example the battery may comprise a rechargeable lithium-ion battery. The components may advantageously be mounted on a motherboard. A more detailed example of circuit components is described below with reference to FIG. 8A and FIG. 8B. A shell or case 23 provides a housing for enclosing the motherboard. The case 23 may advantageously be contoured for ease of holding by a human hand.

In operation, the Bluetooth® transmitter/receiver 32 receives wireless signals 27 including control signals and passes them on to controller 34. In response, the stimulation element 36 may be activated or deactivated. Further, the indicator light 40 may be switched into a plurality of color modes such as red signifying "off," yellow signifying "connecting," and green signifying "connected" modes.

Figure 3:
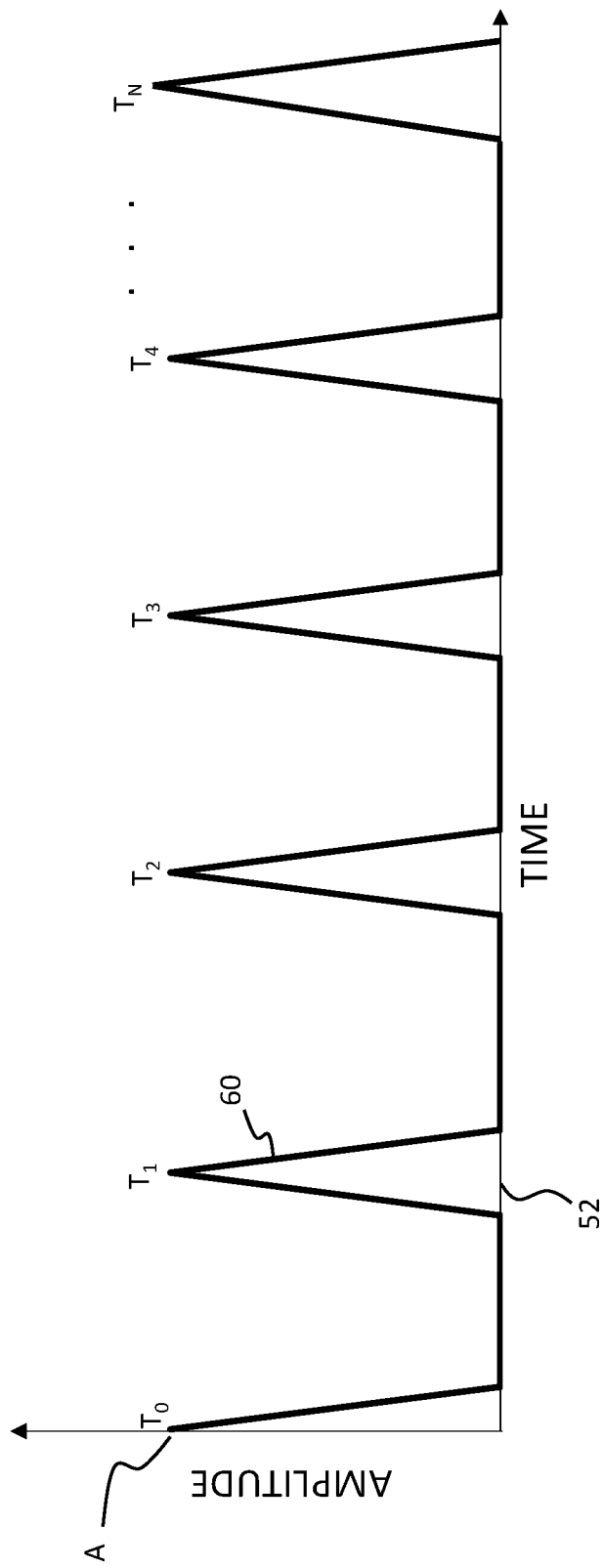
FIG. 3 schematically shows an example of a time sequence of pulses as used in a remotely controlled bilateral alternating tactile stimulation therapeutic system.

Referring now to FIG. 3, an example of a time sequence of pulses as used in a remotely controlled bilateral alternating tactile stimulation therapeutic system is schematically shown. In one example, a pulse control signal 60 may be applied in an alternating fashion to each of the pulsating devices 20. The pulse control signal 60 may be carried by the RF signal 27 and received by the pulsating devices 20. In operation, the pulsating signal 60 may alternate between 0 amplitude or "off" and amplitude A wherein a tactile pulse will be delivered to the subject. Amplitude A must be high enough to activate the stimulation element to produce a tactile response that will be sensed by the subject, as for example when holding a pulsating device 20 in hand, but not so high as to injure or be uncomfortable to the subject. The amplitude A, in one example, may be variably controlled by the therapist or the subject through the applications residing in the mobile devices. It will be understood by those skilled in the art that this is merely one example of a pulse signal waveform and the invention is not so limited. For example, the time between pulses may be as short as 50 ms or as long as 1000 ms or more depending on the response of the subject.

The control waveform 60 includes periodic peaks $T_0$, $T_1$, $T_2$, $T_3$, $T_4$ ... $T_N$ such that single pulse activation signals are delivered in an alternating fashion to the pulsating devices 20 (where N represents an integer number proportional to the length of time of a therapy session). For example, a pulsating device held in the right-hand may pulsate during even subscripted times $T_0$, $T_2$, $T_4$ ... etc. and be turned off during the odd times. A second pulsating device held in the left-hand may pulsate during odd subscripted times $T_1$, $T_3$ ... etc. and be turned off during pulses occurring at the even numbered times, thus supplying alternating bilateral tactile stimulation to the subject. Those skilled in the art having the benefit of this disclosure will recognize that other waveforms and vibration schemes may be used. In another example, the therapist may control the pulsating devices manually by activation icons on the mobile device application. In yet another example, the subject may himself manually control the pulsating devices. Of course, the invention is not limited to single pulse stimuli and the pulsation devices may also operate in other tactile stimulus modes including vibrating at various frequencies.

Figure 4:
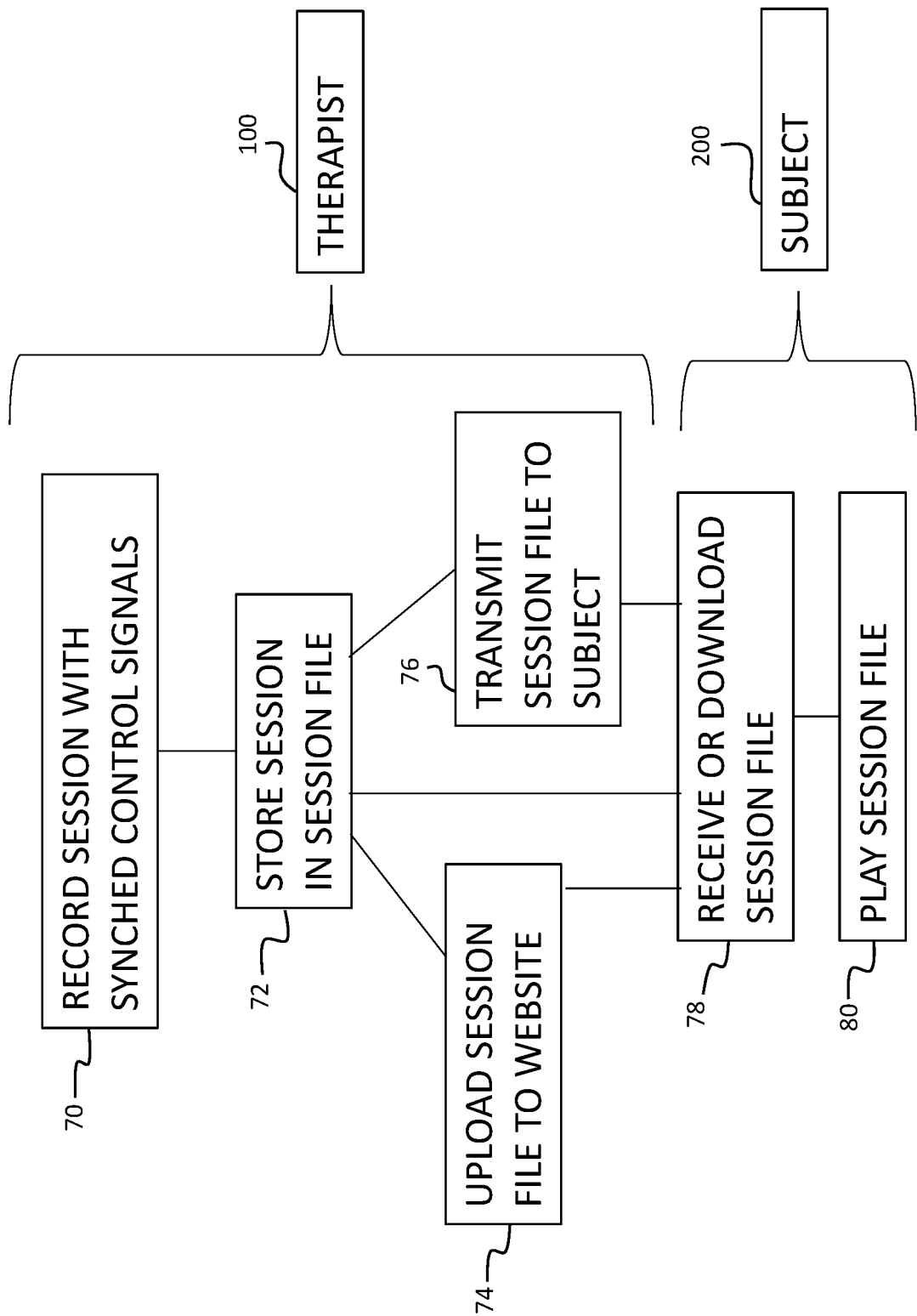
FIG. 4 schematically shows an example of a process for uploading and downloading a therapeutic session with control signals using a remotely controlled bilateral alternating tactile stimulation therapeutic system.

Referring now to FIG. 4, an example of a process for uploading and downloading a therapeutic session with control signals using a remotely controlled bilateral alternating tactile stimulation therapeutic system is schematically shown. In some cases, it may not be possible for a subject to access the Internet as, for example, during a power outage or when the subject is in a very remote location. At the same time, such circumstances may cause a subject to experience severe anxiety that would be ameliorated by bilateral alternating tactile response therapy. Therefore, here provided is a process for storing a therapy session in a website or other processor or mobile device for delivering to the subject as a self-contained therapy session. In this process, a therapist 100 may record a therapy session including synchronized control signals for operating pulsating devices at activity 70. The control signals are synchronized to an audio recording made by the therapist. The recorded session may then be stored in a session file 72. The session file may then be uploaded to a website at activity 74, transmitted as a file to the subject at activity 76, directly transmitted into the subject's mobile device at activity 78, or transmitted using other means known in the art. For example, depending on the size of the file and other factors the file may be transmitted by email, file sharing protocols, cloud storage sharing or the like. When ready, subject 200 may play the session file as indicated at activity 80.

Figure 5:
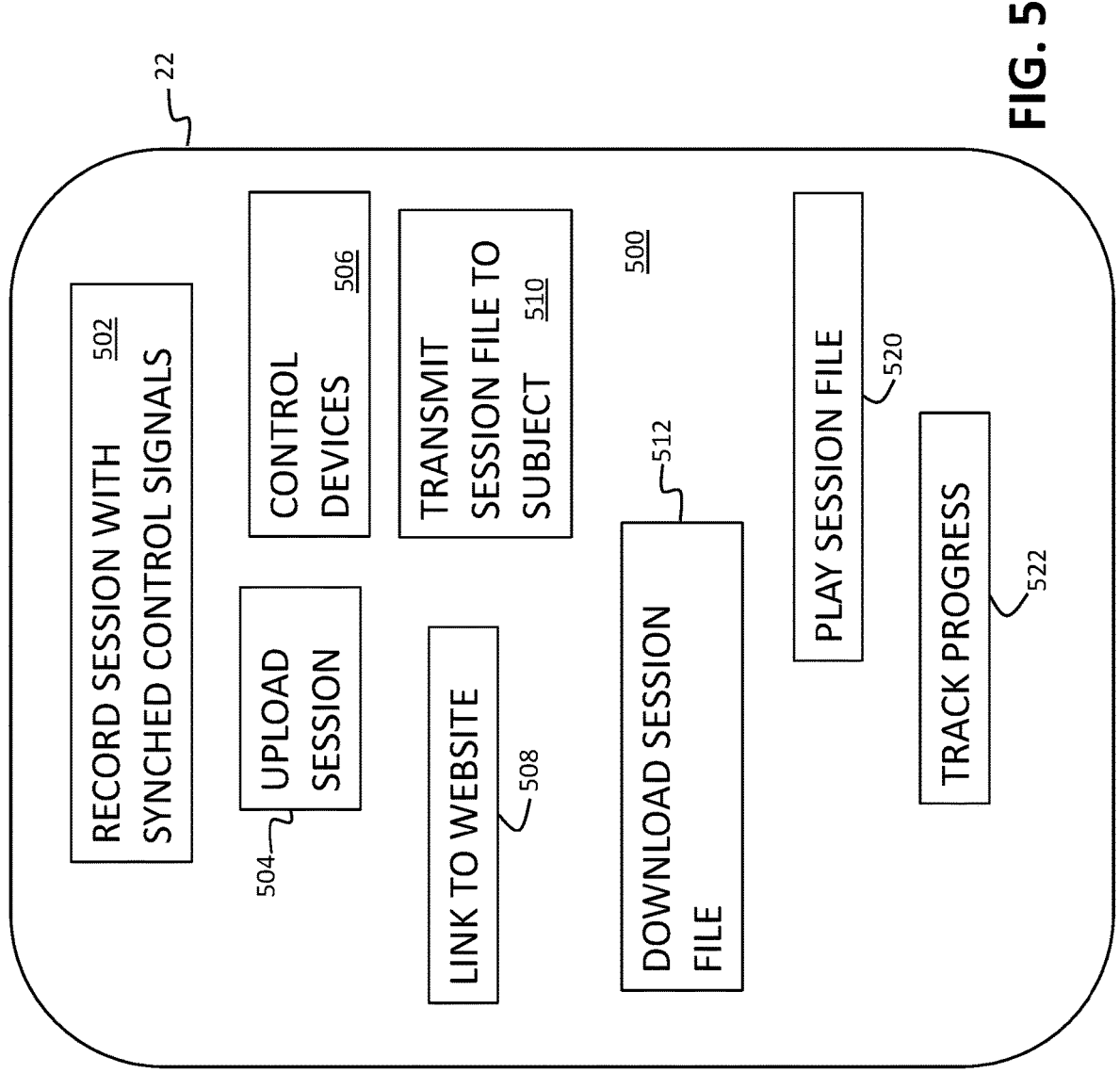
FIG. 5 schematically shows an example of an application control screen for a therapist application for using a remotely controlled bilateral alternating tactile stimulation therapeutic system.

Referring now to FIG. 5, an example of an application control screen for a therapist application for using a remotely controlled bilateral alternating tactile stimulation therapeutic system is schematically shown. A screen 500 may present a plurality of touchscreen sensitive regions represented by icons, text boxes or equivalents for accessing various features of the therapist application. The icons may advantageously include at least a control icon for accessing a control program executed by a processor for recording a session with synchronized control signals 502, an icon for uploading a session 504, an icon for accessing a program executed by a processor for activating pulse signals 506, an icon for linking to a website 508, an icon for accessing a program executed by a processor for transmitting a session file to a subject 510, an icon for accessing a program executed by a processor for downloading a session file 512, an icon for accessing a program executed by a processor for playing a session file 520 and an icon for accessing a program executed by a processor for tracking progress of at least one subject 522. Other common features may be included such as checking status messages, checking push notifications and the like.

Figure 6:
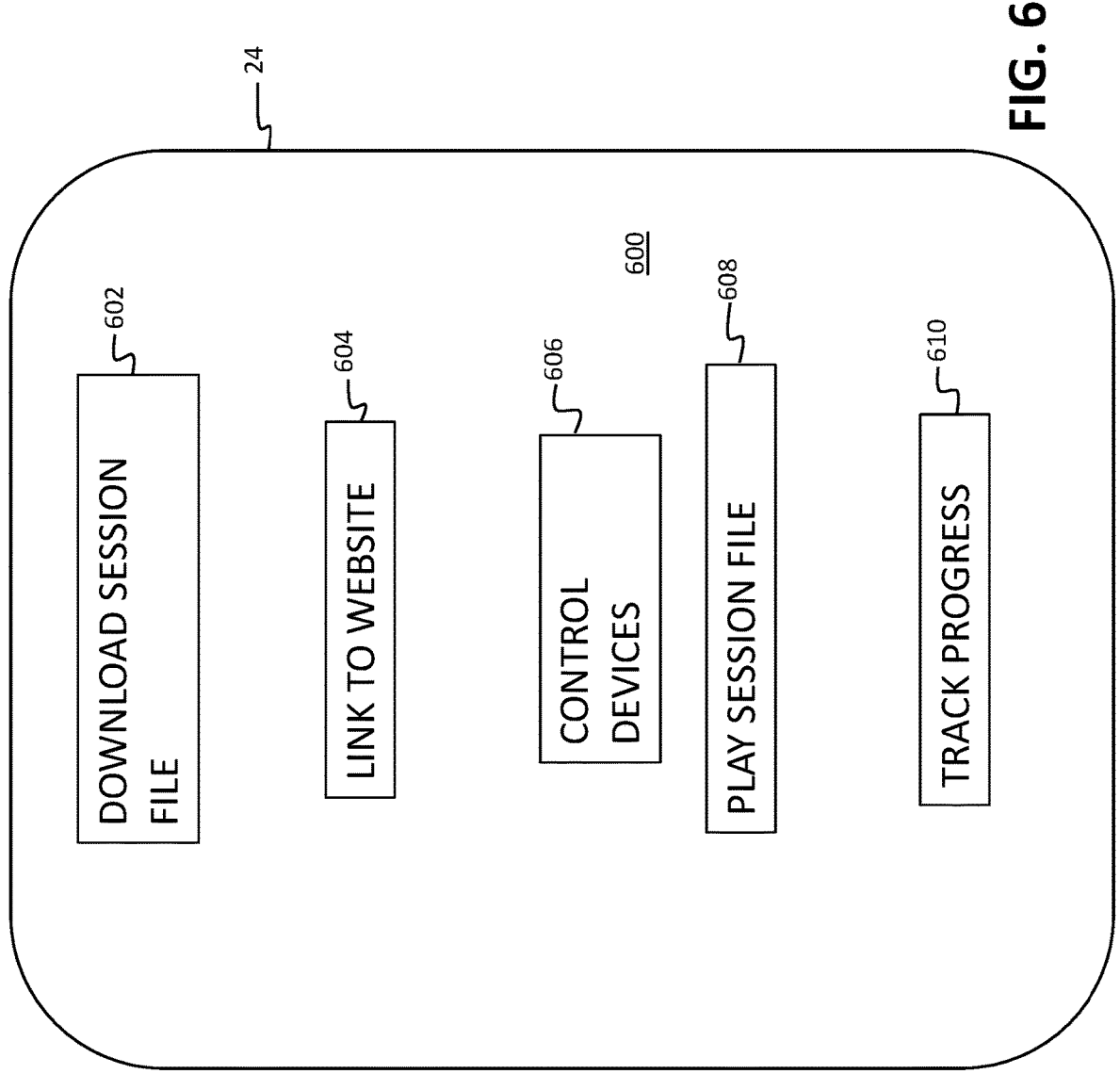
FIG. 6 schematically shows an example of an application control screen for a subject application for using a remotely controlled bilateral alternating tactile stimulation therapeutic system.

Referring now to FIG. 6, an example of an application control screen for a subject application for using a remotely controlled bilateral alternating tactile stimulation therapeutic system is schematically shown. As in the therapist application described above, a screen 600 may present a plurality of touchscreen sensitive regions or icons for accessing various features of the therapist application. The icons may advantageously include at least an icon for accessing a program executed by a processor for downloading a session file 602, an icon for accessing a program executed by a processor for linking to a website 604, an icon for accessing a program executed by a processor for activating pulse signals 606, an icon for accessing a program executed by a processor for playing a session file 608 and an icon for accessing a program executed by a processor for tracking progress of the subject 610. Other common features may be included such as checking status messages, checking push notifications and the like.

Figure 7:
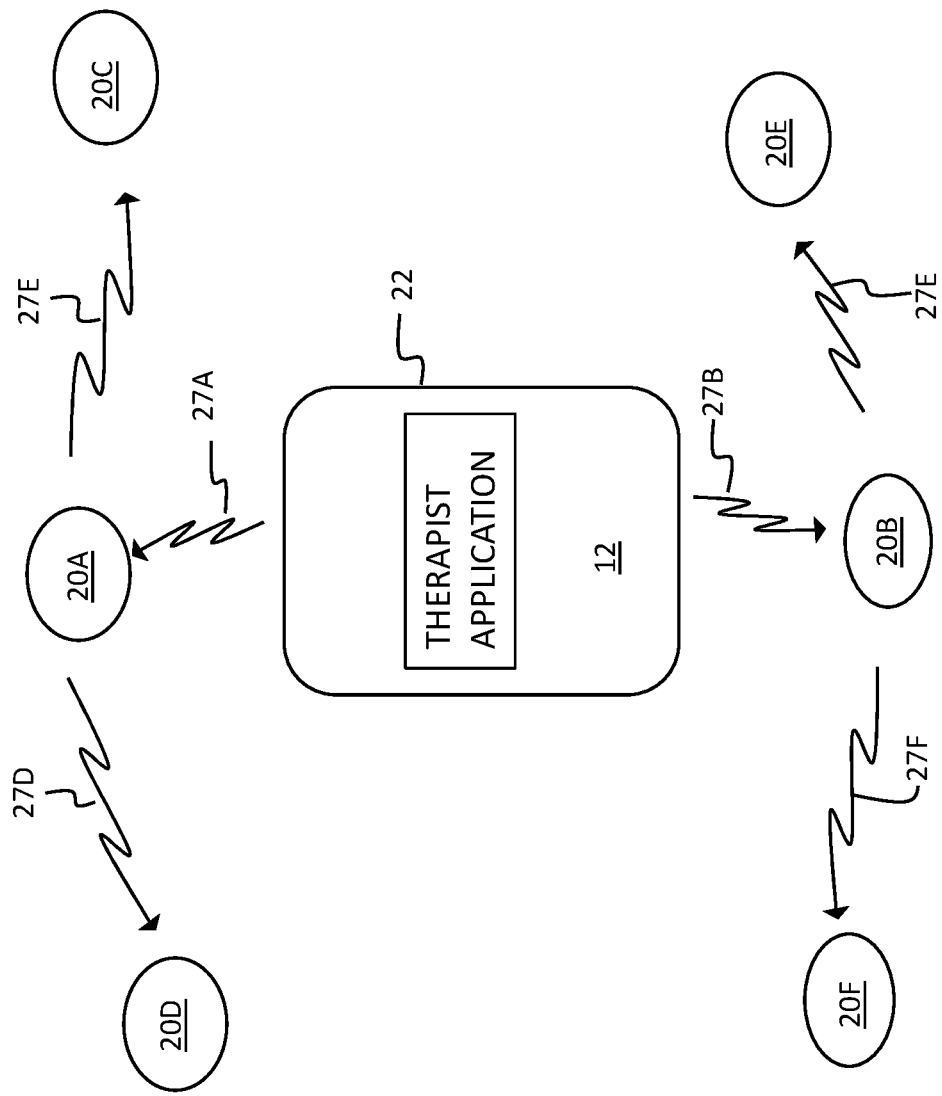
FIG. 7 schematically shows an example of a pair of pulsating devices serving as control units for transmitting pulse signals to a set of additional pulsating devices.

Referring now to FIG. 7, an example of a pair of pulsating devices serving as control units for transmitting pulse signals to a set of additional pulsating devices is schematically shown. In this example, the therapist application 22 transmits pulse control signals 27A, 27B to bilaterally located primary pulsation devices 20A and 20B. Using, for example, Bluetooth® technology, the primary pulsation devices simultaneously transmit the received control signals 27A, 27B to secondary sets of pulsating devices 20C-20F. In this way, a single therapist may be able to conduct a group session using the therapist application 22 and the pulsating devices 20 in a single location.

Figure 8A:
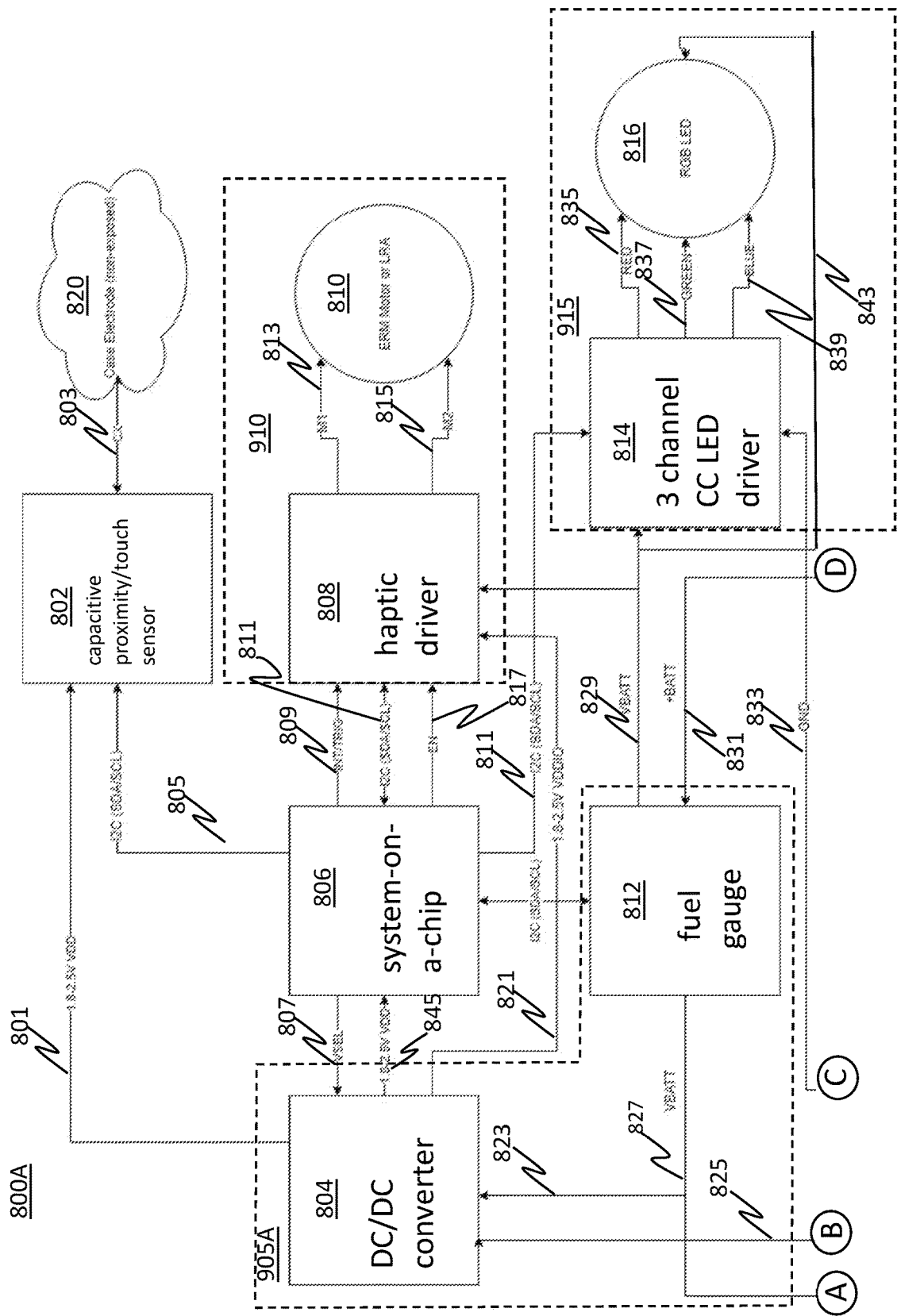
FIG. 8A and FIG. 8B are intended to be pieced together to functionally show an example of a motherboard circuit for controlling a pulsating device.
Figure 8B:
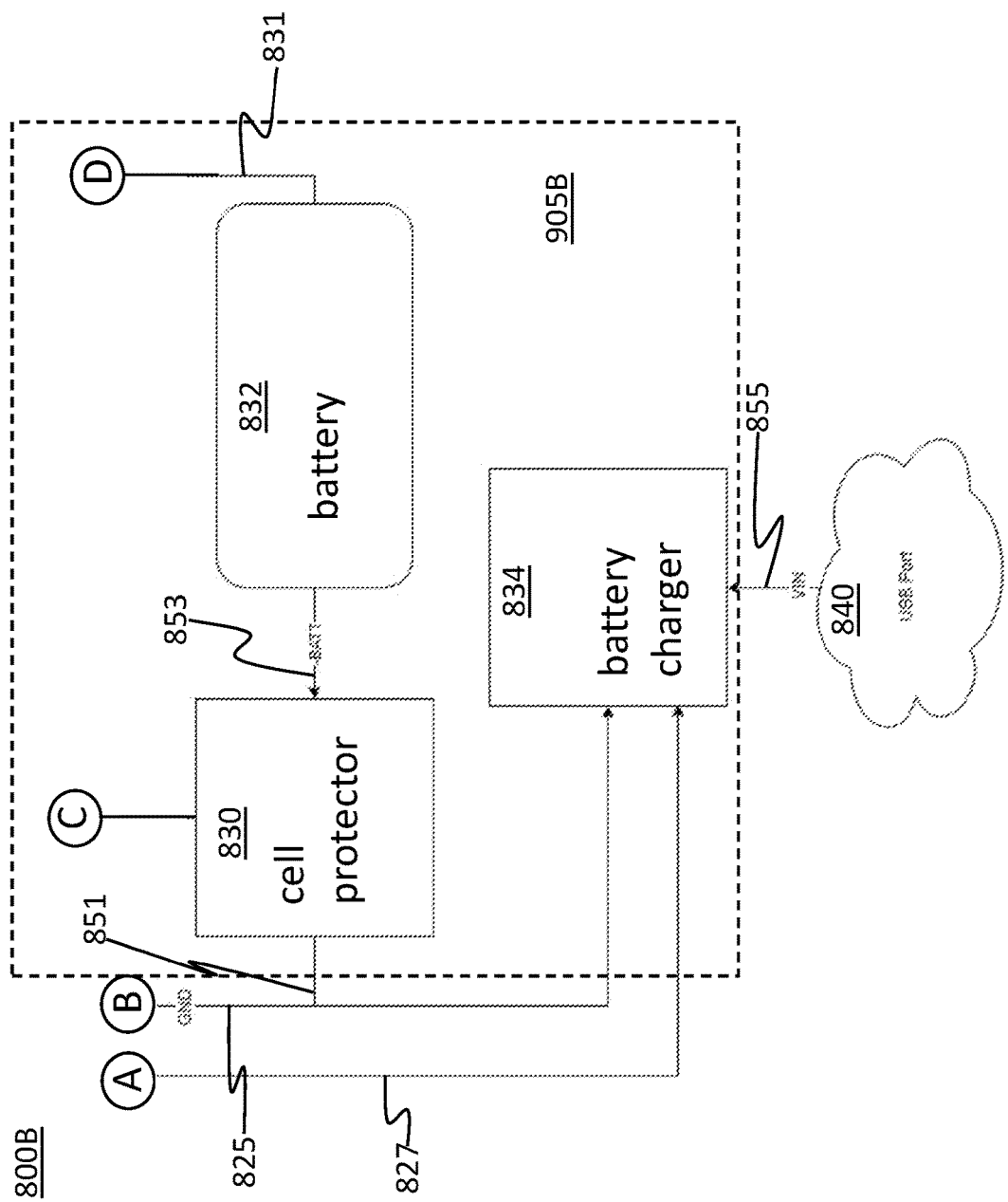

Now referring jointly to FIG. 8A and FIG. 8B, the figures are intended to be pieced together to functionally show an example of a motherboard circuit for controlling a pulsating device. A motherboard 800A, 800B includes a capacitive proximity/touch sensor 802, a DC/DC converter 804, a Bluetooth®-compliant system-on-a-chip 806 (SoC), a haptic driver 808, and ERM motor 810, a fuel gauge circuit 812, a 3 channel CC LED driver 814, and RGB LED 816, a cell protector 830, and ion battery 832 and a battery charger 834. The motherboard circuits are housed within and connected to the shell and outputs of each of the pulsating devices 20.

Referring now more particularly to FIG. 8A, there are four main functional subcircuits comprising the capacitive proximity/touch sensor 802, stimulation subcircuit 910 comprising the haptic driver 808 and motor 810, a status light subcircuit 915 comprising the 3 channel CC LED driver 814 an RGB LED 816, and a power subcircuit 905A, 905B including the battery charger 834, cell protector 830, battery 832, fuel gauge 812, and nano power DC/DC converter 804. The subcircuits all receive information from or supply information to and from the Bluetooth®-compliant system-on-a-chip 806. The system-on-a-chip 806 provides all of the executive functions including control signals to the other subcircuits. The executive functions may reside on the SoC as software applications onboard as firmware or software.

In one example, the power circuit 905A, 905B is electrically coupled to supply power to each of the other subcircuits and the SoC 806. The capacitive proximity/touch sensor 802 is connected to receive power from nano power DC/DC converter 804 through electrical connection 801 and control signals from the SOC 806 through electrical connection 805. The stimulation subcircuit 910 receives triggering signals through electrical connection INT/TRIG 809. In operation, INT/TRIG 809 transmits interrupts or trigger signals in the form of pulses as shown in FIG. 3 received by the haptic driver 808. Electrical connection 811 may be a I2C (SDA/SCL) bus. I2C is a serial protocol for two-wire interface to connect low-speed devices like microcontrollers, EEPROMs, A/D and D/A converters, I/O interfaces, and other similar peripherals in onboard systems. An enable signal 817 may be transmitted through electrical connection 817 from the SOC 806 to the haptic driver 808. Power is applied to the haptic driver 808 from the DC/DC converter 804 through electrical power line 821.

The haptic driver 808 is connected to drive the ERM motor 810 or a linear resonant actuator (LRA), depending on the type of haptic stimulator employed, using electrical connections 813, 815. If an ERM motor is used the haptic driver outputs DC signals, if an LRA is used the haptic driver outputs AC signals. The capacitive proximity touch sensor 802 is connected to transmit and receive electrical signals from the case electrode 820. The case electrode 820 is part of the case of a stimulation device 20. The status light indicator subcircuit 915 includes the 3 channel CC LED driver 814 which is connected by powerline 829 to the fuel gauge circuit 812. RGB LED receives red, green, and blue signal information from the LED driver 14 BR electrical connections 835, 837, and 839, respectively. Power to the RGB LED 816 is routed through electrical connection 843. Control signals are supplied by SOC 806 through electrical connection 811 to the 3 channel CC LED driver 814.

Referring now particularly to FIG. 8B, a second portion of the power circuit 905B includes the cell protector 830, battery 832, and the battery charger 834. In one example, the battery charger 834 may receive a charge from and external USB port 840 connected to or part of a personal computer, battery charger or the like. Battery charger 834 receives charging information from the nano power DC/DC converter 804 and the fuel gauge 812 through electrical connections 825, 827. In one example, line 825 may be a ground which is applied by connection 851 to cell protector 830 and 825 to the battery charger 824. The battery 832 is connected to fuel gauge circuit 812 by a positive terminal connection 831. The battery 832 is also connected electrically to cell protector 830 by electrical connection 853.

Motherboard Example

SoC:

One example embodiment was built around the system-on-a-chip 806 where the selected SoC was a Nordic Semiconductor model number nRF52832. The nRF52 series supports Bluetooth® standards BLE5.0 as well as BLE4.2/4.1/4.0 and ANT protocols and has an ARM Cortex M4F processor at 64 Mhz. Additionally, the nRF52832 has an onboard NFC Class-A tag which can be programed by the device, a feature which is useful for pairing techniques such as out of band pairing (OOB), or for conveying device information such as serial and model numbers, as well as, firmware information such as build version or mesh address.

The battery selected was a coin cell rechargeable lithium battery. The RJD2032C1 is a CR2032 form factor Lithium nickel manganese cobalt oxide (Li-NMC) cell with a rated capacity of 85 mAh and a nominal voltage of 3.7V. A brief charge time was a desirable feature and since this battery is designed to charge at 0.5C or 40 mA, this met the desired parameters with a charge time of approximately two hours. The RJD2032 is specifically designed for wearables and IoT devices and is UL1642-MH28281 certified for safety.

Battery Charging:

Battery charging was designed to be accomplished using a linear constant current/constant voltage charger IC which includes automatic charge termination (1/10 IC) and over temperature protection. The charge current is programmed using a resistor, the device is set at 40 mA using a 25 kOhm resistor. Charge status is indicated by a red charging LED that turns off after charge is terminated and the charge is supplied as 5 volts from the micro usb charge port on the device.

Battery Monitoring:

As the device is wireless and battery powered, battery monitoring helps assure system reliability. Additionally, battery status monitoring is typically considered standard with modern devices. To achieve better performance a commercially available fuel gauge integrated circuit (IC) was used (Maxim Integrated MAX17055). The fuel gauge IC employs a combination of voltage measurement and coulomb counting to provide a more accurate battery measurement. The MAX17055 employs a learning algorithm to characterize the battery on the fly; this algorithm improves characterization with each charge-discharge cycle of the battery and can adapt the algorithm as the battery ages or is replaced. The fuel gauge provides common battery metrics such as state of charge, voltage, current and active power, and also time-to-empty and time-to-full predictions and temperature.

Bus Power Regulator:

The SoC, as well as several peripherals on the device, have maximum input voltages of 3.6 v and so, since a fully charged lithium ion cell has a voltage of 4.2-4.4 v, a voltage regulator is required. The DC-DC converter selected for this device was Texas Instruments model number TPS82740A, a fully integrated power converter micromodule capable of stable operation with no external components. The TPS82740 improves light load efficiency with a PWM/PFM hybrid operating model: at heavy loads the converter operates on pulse width modulation (PWM) in continuous conduction mode (CCM) and at light loads the converter operates on pulse frequency modulation (PFM) in discontinuous conduction mode (DCM) which greatly reduces switching frequency and thus quiescent current, allowing the converter to operate above 90% efficiency from 10 µA-200 mA. This is a substantial improvement over a fixed 43% efficiency with a linear regulator. The integrated micromodule results in a net reduction of components as the alternative LDO regulators require input and output capacitors for stability.

LED Indicator:

In one example, the RGB status light 816 used was approximately ⅛" in diameter; a 3528 LED with a diffuse lens was selected for improved aesthetics. The three channel cc LED driver selected was an ISSI® model IS31FL3193D integrated circuit. This IC prevents chromaticity and brightness shifts due to battery voltage and also allows for pattern effects such as "breathing", "color fading" and flashing to be scripted on the driver IC, thereby reducing CPU workload. Additionally, this selection reduced component count by five over discrete transistor/resistor solutions and allows for five programmable references current bands (5-42 mA), such that brightness can be adjusted without dithering color depth. Each channel has 8-bit current control, allowing for full 24-bit color at five brightness levels.

Touch Sensing:

In contrast to most current BLS systems that rely on mechanical power switches, the system disclosed herein provides a sleeker and more modern device appearance and interactivity. The sensor selected for the device was an Azoteq IQS231A single channel self-capacitance controller. It is configured for a sample rate of 4 sps but can be reconfigured, via software, up to 100 sps (at higher power consumption). The theoretical power consumption is 9-12.5 µW (depending on bus voltage setting) at the 4 sps sample rate.

Haptic Actuator:

The current BLS products on the market rely on eccentric rotating mass (ERM) type vibration actuators. ERM actuators are a proven technology with simple control systems, but have substantial negatives: they are mechanically complex with many points of failure and have consumable components (such as brushes and bearings) that greatly limit the effective service life and cause increased noise and power consumption. The simulation device 20, in contrast to the state-of-the-art, uses linear resonant actuators (LRAs) which are mechanically much simpler, consisting of only of a coil, a spring, and magnet mass. As a result of their mechanical simplicity they have much longer or, in some cases, virtually infinite service lives and are also significantly more energy efficient than ERMs. The range of haptic effects that can be produced with LRAs is much wider than ERMs since they are electrically. rather than mechanically, commutated.

Haptic Controller:

Since ERM actuators require a simple constant DC input and do not require polarity reversal, they can be controlled with a single transistor. In contrast, LRAs require AC drive, a minimum of 4 transistors in an H-Bridge configuration are needed to operate the device; additionally, this is complicated by the high Q factor of LRAs, often having an operating bandwidth of only a few hundred millihertz and so a control system must have very precise timing to effectively drive an LRA. To accomplish this with a minimum number of parts, a highly integrated haptic driver IC was selected. There are two common haptic driver chips for LRAs; TI's DRV2605 and Dialog Semi's DA7280; the DA7280 was initially chosen due to manufacturing constraints as the system planned for printing PCBs had a minimum allowable pad pitch of 0.65 mm and the DRV2605 is only offered in MSOP-10 (e=0.5 mm) or WLCSP-9 (e=0.4 mm), while the DA7280 was offered in QFN-12 (e=0.65 mm) and WLCSP-9 (e=0.4 mm). However, after close comparison it became evident that the DA7280 offered significant advantages over the drv26051. The sleep current of the DA7280 is over an order of magnitude lower than that of the drv2605 (360 nA vs. 4.1 µA) and the DA7280 has a programable waveform library, whereas the drv2605 has only the pre-loaded effects library. Additionally, the DA7280 allows for more comprehensive diagnostics for both actuator and system.

Programming

In one example, a smartphone application was written in Ionic coding language that offers a cross platform framework, reducing development time and creating a consistent user interface for both Android and iOS. Google Firebase was selected as the web technology as its pricing structure is favorable for a small user base, and it interfaces well with Ionic, allows cross registration to support multiple accounts and allows for https-supporting secure HIPAA compliant communication. One skilled in the art having the benefit of this disclosure and instructed by the functional description described herein would be able to prepare any required software programs using available technology and know-how. The programs are accessed by activating the touch-screen icons or textboxes as described above.

Figure 9:
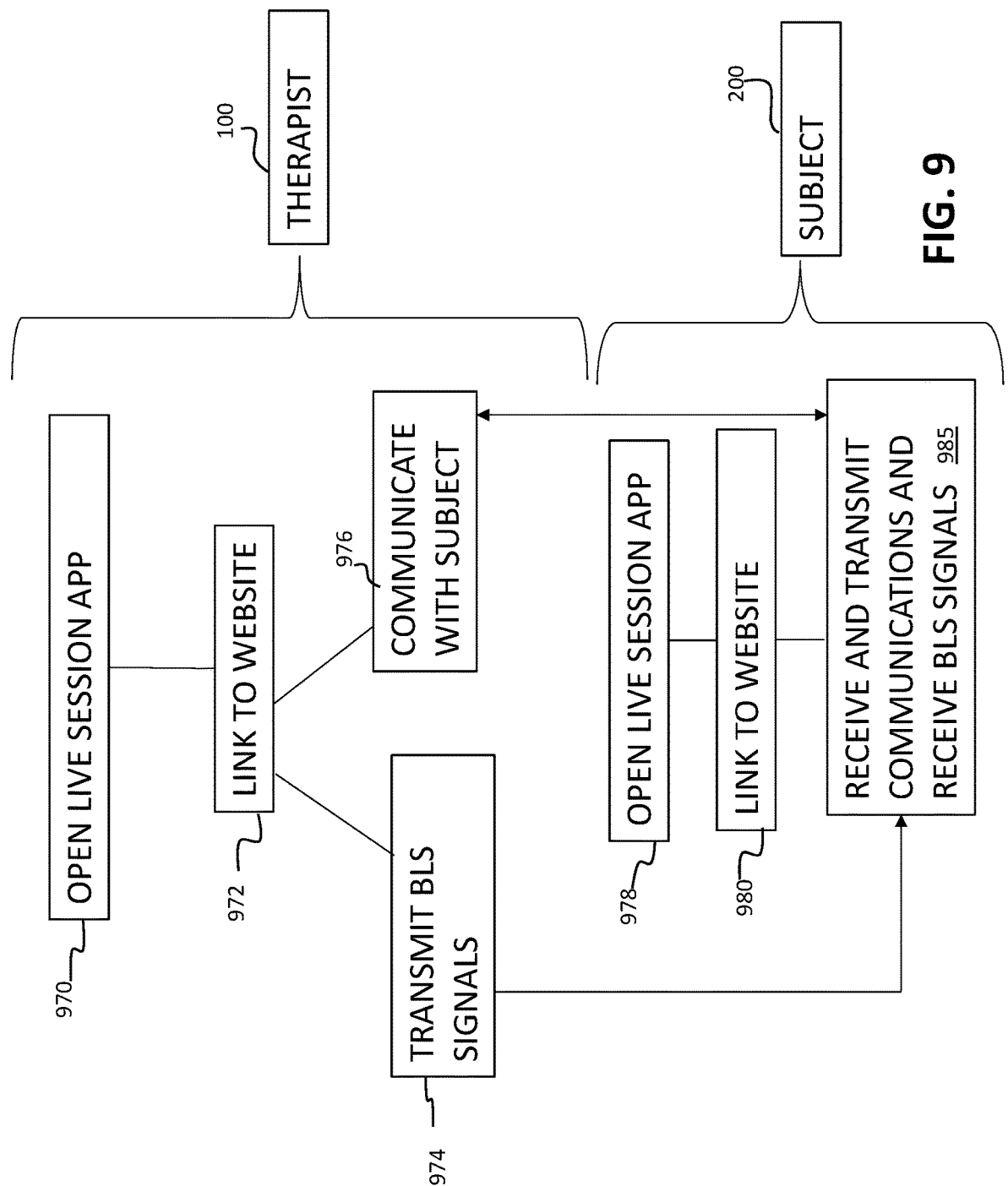
FIG. 9 schematically shows an example of a process for live streaming a therapeutic session with control signals using a remotely controlled bilateral alternating tactile stimulation therapeutic system.

Referring now to FIG. 9, an example of a process for live streaming a therapeutic session with control signals using a remotely controlled bilateral alternating tactile stimulation therapeutic system is schematically shown. The process includes beginning a session by opening a live session application 970. A live session application 970 resides in the mobile device or may be accessed through the website. A link to the website is established at 972. Once the link to the website is established a therapist 100 may both communicate with the subject by audio or video communications and also send BLS signals as needed. The subject 200 will, when the live session begins, open live session application 978 residing in the subject's mobile device or access by the mobile device in the website through a link established at 980. The subject 200 then receives and transmits communications and receives BLS signals as the session progresses 985.

In one example of a bilateral alternating tactile stimulation therapeutic system the system includes an Internet web page; a first mobile device, at a first location, configured to access the Internet web page, a first processor, onboard the first mobile device, the first processor being programmed to execute a first application for transmitting audio information and pulse control information including alternating pulsation signals for uploading to the Internet web page; a second mobile device, at a second location remote from the first location, adapted to connect to the Internet web page; a second processor, onboard the second mobile device, programmed to execute a second application for receiving the audio information and the pulse control information in a streaming or live mode; a first pair of pulsating devices wirelessly coupled to the second mobile device; and where the second processor is programmed to enable a subject to hear the audio information through the mobile device and transmit the alternating pulsation signals to the pair of pulsating devices.

In another example, the Internet web page includes computer software programs for uploading and downloading.

In another example, the audio information and pulse control information are transmitted using radio frequency signals.

In another example, the pair of pulsating devices include a receiver, a controller electrically coupled to the receiver; a rechargeable battery electrically coupled to the controller and the receiver; a stimulation element electrically coupled to the controller and the rechargeable battery; and a status light electrically coupled to the controller and the rechargeable battery.

In another example, the controller comprises a microprocessor or system-on-a-chip.

In another example, the status light emanates a plurality of color modes.

In another example, the pulse control information comprises a time sequence of pulses.

In another example, the first mobile device has an application control screen for a therapist application for using a remotely controlled bilateral alternating tactile stimulation therapeutic system comprising a control icon for recording a session with synchronized control signals; an upload icon for uploading a session; an activation icon for activating pulse signals; a linking icon for linking to a website; a transmission icon for transmitting a session file to a subject; a download icon for downloading a session file; a play icon for playing a session file; and a tracking icon for tracking progress of at least one subject.

In yet another example, the second mobile device has an application control screen for a subject application for using a remotely controlled bilateral alternating tactile stimulation therapeutic system comprising a linking icon for linking to a website; a download icon for downloading a session file; a play icon for playing a session file; and a tracking icon for tracking progress of the subject.

In another example, the system further includes a plurality of additional pairs of pulsating devices wirelessly coupled to the first pair of pulsating devices.

In another example, a method for pre-recording and delivering a therapeutic session including audio information and control signals includes the acts of downloading a first bilateral alternating tactile stimulation therapeutic system application on a first mobile device; operating the first mobile device to execute the first application to record a therapy session including audio information and synchronized control signals for operating pulsating devices; storing the recorded session in a session file; uploading the session file to a website, transmitting the session file into another mobile device; downloading a second bilateral alternating tactile stimulation therapeutic system application on a second mobile device; receiving the session file through the second application in the second mobile device; operating the second application to play the session file on the second mobile device to listen to the audio information; and wirelessly controlling a first pair of pulsating devices with the synchronized control signals.

In another example, the method further includes wirelessly connecting at least a second pair of pulsating devices to the first pair of pulsating devices; and controlling the at least second pair of pulsating devices through the first pair of pulsating devices.

In another example a method for live streaming a therapeutic session including audio information and bilateral alternating tactile stimulation signals, where the method includes the acts of operating a first mobile device to open a first live session application by a therapist; establishing a first link to a website; once the first link to the website is established, communicating with a subject by audio or video communications; transmitting a series of BLS signals by the therapist; opening a second live session application; establishing a second link to the website; receiving and transmitting communications by the subject; and receiving the BLS signals by the subject through the subject's mobile device.

In another example the first live session application resides in the first mobile device or may be accessed through the website.

In yet another example, the second live session application resides in the subject's mobile device or is accessed by the subject's mobile device in the website established through the second link.

Certain exemplary embodiments of the invention have been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The teachings of the following publications are incorporated by reference herein.
1. Amano, T., & Toichi, M. (2016). The Role of Alternating Bilateral Stimulation in Establishing Positive Cognition in EMDR Therapy: A Multi-Channel Near-Infrared Spectroscopy Study. *PloS one,* 11(10), e0162735. doi:10.1371/journal.pone.0162735
2. Bandelow, B., & Michaelis, S. (2015). Epidemiology of anxiety disorders in the 21st century. *Dialogues in clinical neuroscience,* 17(3), 327-335.
3. Bisson J, Ehlers A, Matthews R, Pilling S, Richards D, Turner S. Psychological treatments for chronic post-traumatic stress disorder: Systematic review and meta-analysis. British Journal of Psychiatry. 2007; 190: 97-104. 10.1192/bjp.bp.106.021402
4. Ohira H, Nomura M, Ichikawa N, Isowa T, Iidaka T, Sato A, et al. Association of neural and physiological responses during voluntary emotion suppression. Neuro Image. 2006; 29-3: 721-733. 10.1016/j.neuroimage.2005.08.047
5. Serin A., Hageman N, Kade E, The Therapeutic Effect of Bilateral Alternating Stimulation Tactile Form Technology on the Stress Response. Journal of Biotechnology and Biomedical Science 2018-1(2):42-47.

What is claimed is:
1. A bilateral alternating tactile stimulation therapeutic system comprising:
an Internet web page;
a first mobile device, at a first location, configured to access the Internet web page;
a first processor, onboard the first mobile device, the first processor being programmed to execute a first application for transmitting audio information and pulse control information including alternating pulsation signals for uploading to the Internet web page;
the first processor being programmed to execute an application that records a therapy session, where the therapy session is synchronized with the alternating pulsation signals;
a second mobile device, at a second location remote from the first location, adapted to connect to the Internet web page;
a second processor, onboard the second mobile device, programmed to execute a second application for receiving the audio information and the pulse control information in a streaming mode;
a first pair of pulsating devices wirelessly coupled to the second mobile device; and
where the second processor is programmed to enable a subject to hear the audio information through the mobile device and transmit the alternating pulsation signals to the pair of pulsating devices.

2. The system of claim 1 wherein the Internet web page includes computer software programs for uploading and downloading.

3. The system of claim 1 wherein the audio information and pulse control information are transmitted using radio frequency signals.

4. The system of claim 1 wherein the pair of pulsating devices comprise:
a receiver;
a controller electrically coupled to the receiver;
a rechargeable battery electrically coupled to the controller and the receiver;
a stimulation element electrically coupled to the controller and the rechargeable battery; and
a status light electrically coupled to the controller and the rechargeable battery.

5. The system of claim 4 wherein the controller comprises a microprocessor or system-on-a-chip.

6. The system of claim 4 wherein the status light emanates a plurality of color modes.

7. The system of claim 1 wherein the pulse control information comprises a time sequence of pulses.

8. The system of claim 1 wherein the first mobile device has an application control screen for a therapist application for using a remotely controlled bilateral alternating tactile stimulation therapeutic system comprising:
a control icon for accessing a recording application executed by the first processor to record the therapy session synchronized with the alternating pulsation signals;
an upload icon for accessing an upload application executed by the first processor to upload a session;
an activation icon for accessing an activation application executed by the first processor to activate the alternating pulsation signals;
a first linking icon for accessing linking to a website;
a transmission icon for accessing a transmitting program executed by the first processor to transmit a session file to a subject;
a first download icon for accessing a first downloading program executed by the first processor to download a session file;
a first play icon for accessing a first play program executed by the first processor to play a session file; and
a first tracking icon for accessing a first tracking program executed by the first processor to track progress of at least one subject.

9. The system of claim 1 wherein the second mobile device has an application control screen for a subject application for using a remotely controlled bilateral alternating tactile stimulation therapeutic system comprising:
- a second mobile device linking icon for accessing linking to a website;
- a second mobile device download icon for accessing a second mobile device downloading program executed by the second processor to download a session file;
- a second mobile device play icon for accessing a second mobile device play program executed by the second processor to play the recorded therapy session; and
- a second mobile device tracking icon for accessing a second mobile device tracking program executed by the second processor to track progress of at least one subject.

10. The system of claim 1 further comprising a plurality of additional pairs of pulsating devices wirelessly coupled to the first pair of pulsating devices.

11. A bilateral alternating tactile stimulation therapeutic system comprising:
- an Internet web page;
- a first mobile device, at a first location, configured to access the Internet web page;
- a first processor, onboard the first mobile device, the first processor being programmed to execute a first application for transmitting audio information and pulse control information including alternating pulsation signals for uploading to the Internet web page;
- a second mobile device, at a second location remote from the first location, adapted to connect to the Internet web page;
- a second processor, onboard the second mobile device, programmed to execute a second application for receiving the audio information and the pulse control information in a streaming or live mode;
- a first pair of pulsating devices wirelessly coupled to the second mobile device;
- where the second processor is programmed to enable a subject to hear the audio information through the mobile device and transmit the alternating pulsation signals to the pair of pulsating devices; and
- wherein the first mobile device has an application control screen for a therapist application for using a remotely controlled bilateral alternating tactile stimulation therapeutic system including
  - a control icon for accessing a recording application executed by the first processor to record a session with synchronized control signals;
  - an upload icon for accessing an upload application executed by the first processor to upload a session,
  - an activation icon for accessing an activation application executed by the first processor to activate pulse signals,
  - a first linking icon for accessing linking to a website,
  - a transmission icon for accessing a transmitting program executed by the first processor to transmit a session file to a subject,
  - a first download icon for accessing a first downloading program executed by the first processor to download a session file,
  - a first play icon for accessing a first play program executed by the first processor to play a session file, and
  - a first tracking icon for accessing a first tracking program executed by the first processor to track progress of at least one subject.

12. The system of claim 11 wherein the second mobile device has an application control screen for a subject application for using a remotely controlled bilateral alternating tactile stimulation therapeutic system comprising:
- a second mobile device linking icon for accessing linking to a website;
- a second mobile device download icon for accessing a second mobile device downloading program executed by the second processor to download a session file;
- a second mobile device play icon for accessing a second mobile device play program executed by the second processor to play the recorded therapy session; and
- a second mobile device tracking icon for accessing a second mobile device tracking program executed by the second processor to track progress of at least one subject.

13. The system of claim 11 further comprising a plurality of additional pairs of pulsating devices wirelessly coupled to the first pair of pulsating devices.

14. A bilateral alternating tactile stimulation therapeutic system comprising:
- an Internet web page;
- a first mobile device, at a first location, configured to access the Internet web page;
- a first processor, onboard the first mobile device, the first processor being programmed to execute a first application for transmitting audio information and pulse control information including alternating pulsation signals for uploading to the Internet web page;
- a second mobile device, at a second location remote from the first location, adapted to connect to the Internet web page;
- a second processor, onboard the second mobile device, programmed to execute a second application for receiving the audio information and the pulse control information in a streaming or live mode;
- a first pair of pulsating devices wirelessly coupled to the second mobile device;
- where the second processor is programmed to enable a subject to hear the audio information through the mobile device and transmit the alternating pulsation signals to the pair of pulsating devices; and
- wherein the second mobile device has an application control screen for a subject application for using a remotely controlled bilateral alternating tactile stimulation therapeutic system including
  - a second mobile device linking icon for accessing linking to a website,
  - a second mobile device download icon for accessing a second mobile device downloading program executed by the second processor to download a session file,
  - a second mobile device play icon for accessing a first second mobile device play program executed by the second processor to play the recorded therapy session, and
  - a second mobile device tracking icon for accessing a second mobile device tracking program executed by the second processor to track progress of at least one subject.

15. The system of claim 14 further comprising a plurality of additional pairs of pulsating devices wirelessly coupled to the first pair of pulsating devices.

* * * * *